(12) United States Patent
Becker et al.

(10) Patent No.: US 10,766,839 B2
(45) Date of Patent: Sep. 8, 2020

(54) PROCESS FOR CONVERTING OLEFINS TO ALCOHOLS, ETHERS, OR COMBINATIONS THEREOF

(71) Applicant: Dow Technology Investments LLC, Midland, MI (US)

(72) Inventors: Michael C. Becker, Dickinson, TX (US); Michael A. Brammer, Freeport, TX (US); Jason F. Giles, Missouri City, TX (US); Glenn A. Miller, South Charleston, WV (US); George R. Phillips, South Charleston, WV (US); Rick B. Watson, Missouri City, TX (US); Stephane Wambergue, London (GB); Martin Lucas Smidt, London (GB)

(73) Assignee: Dow Technology Investments LLC, Midland, MI (US)

( * ) Notice: Subject to any disclaimer, the term of this patent is extended or adjusted under 35 U.S.C. 154(b) by 18 days.

(21) Appl. No.: 16/076,734

(22) PCT Filed: Feb. 10, 2017

(86) PCT No.: PCT/US2017/017325
§ 371 (c)(1),
(2) Date: Aug. 9, 2018

(87) PCT Pub. No.: WO2017/139543
PCT Pub. Date: Aug. 17, 2017

(65) Prior Publication Data
US 2019/0047930 A1 Feb. 14, 2019

Related U.S. Application Data

(60) Provisional application No. 62/294,092, filed on Feb. 11, 2016.

(51) Int. Cl.
*C07C 29/141* (2006.01)
*C07C 41/01* (2006.01)
(Continued)

(52) U.S. Cl.
CPC ............ *C07C 29/141* (2013.01); *C07C 41/01* (2013.01); *C07C 45/50* (2013.01); *C07C 45/505* (2013.01);
(Continued)

(58) Field of Classification Search
CPC combination set(s) only.
See application file for complete search history.

(56) References Cited

U.S. PATENT DOCUMENTS 2,578,724 A 12/1951 Mertzweiller
3,415,906 A 12/1968 Shepard et al.
(Continued)

FOREIGN PATENT DOCUMENTS

DE 896638 11/1953
DE 10035370 3/2001
(Continued)

OTHER PUBLICATIONS

Kohlpaintner, Christian, et al., "Aqueous biphasic catalysis: Ruhrchemie/Rhône-Poulenc oxo process," Applied Catalysis A: General 221, 2001, pp. 219-225.
(Continued)

*Primary Examiner* — Ellen M McAvoy
*Assistant Examiner* — Chantel L Graham

(57) ABSTRACT

The present invention relate to processes for converting olefins to alcohols, ethers, or combinations thereof that are suitable for use as a gasoline additive. In one embodiment, the process comprises (a) receiving a feed stream, wherein the feed stream comprises one or more olefins having 2 to 5 carbon atoms in an amount of up to 80% by weight based on
(Continued)

the weight of the feed stream; (b) hydroformylating the feed stream in the presence of a catalyst to convert at least 80% of the olefins from the feed stream to oxygenates; (c) separating a product stream from step (b) into an oxygenate stream and a stream comprising unreacted olefins, inerts, the catalyst, and the remaining oxygenates; and (d) treating the oxygenate stream to convert a plurality of the oxygenates into at least one of an alcohol, an ether, or combinations thereof is suitable for use as a gasoline additive.

14 Claims, 1 Drawing Sheet

(51) Int. Cl.
*C07C 45/50* (2006.01)
*C10L 1/182* (2006.01)
*C10L 1/185* (2006.01)

(52) U.S. Cl.
CPC ........... *C10L 1/1824* (2013.01); *C10L 1/1852* (2013.01); *C10L 2200/0423* (2013.01); *C10L 2270/023* (2013.01); *Y02P 20/582* (2015.11)

(56) References Cited

U.S. PATENT DOCUMENTS

| | | |
|---|---|---|
| 3,527,809 A | 9/1970 | Pruett et al. |
| 4,148,830 A | 4/1979 | Pruett et al. |
| 4,247,486 A | 1/1981 | Brewester et al. |
| 4,248,802 A | 2/1981 | Kuntz |
| 4,283,562 A | 8/1981 | Billig et al. |
| 4,287,370 A | 9/1981 | Harris et al. |
| 4,299,990 A | 11/1981 | Tummes et al. |
| 4,567,302 A | 1/1986 | Sivaramakrishnan |
| 4,567,306 A | 1/1986 | Dennis et al. |
| 4,599,206 A | 7/1986 | Billig et al. |
| 4,668,651 A | 5/1987 | Billig et al. |
| 4,711,968 A * | 12/1987 | Oswald ................ C07C 29/16 568/454 |
| 4,717,775 A | 1/1988 | Billig et al. |
| 4,749,724 A | 6/1988 | Quarderer et al. |
| 4,774,361 A | 9/1988 | Maher et al. |
| 4,835,299 A | 5/1989 | Maher et al. |
| 4,960,960 A | 10/1990 | Harrison et al. |
| 4,969,953 A | 11/1990 | Miyazawa et al. |
| 5,093,535 A | 3/1992 | Harrison et al. |
| 5,102,505 A | 4/1992 | Sorensen |
| 5,110,990 A | 5/1992 | Blessing et al. |
| 5,191,129 A | 3/1993 | Irvine |
| 5,288,918 A | 2/1994 | Maher et al. |
| 5,312,996 A | 5/1994 | Packett |
| 5,430,194 A | 7/1995 | Barner et al. |
| 5,681,473 A | 10/1997 | Miller et al. |
| 5,728,893 A | 3/1998 | Becker et al. |
| 5,731,472 A | 3/1998 | Leung et al. |
| 5,741,942 A | 4/1998 | Bryant et al. |
| 5,741,944 A | 4/1998 | Bryant et al. |
| 5,744,649 A | 4/1998 | Bryant et al. |
| 5,929,289 A | 7/1999 | Abatjoglou et al. |
| 6,100,432 A | 8/2000 | Borgel et al. |
| 6,265,619 B1 | 7/2001 | de Rijke |
| 6,444,863 B2 | 9/2002 | Ueda et al. |
| 6,555,716 B2 | 4/2003 | Protzmann et al. |
| 6,864,391 B2 | 3/2005 | Krokoszinski et al. |
| 6,969,777 B2 | 11/2005 | Walz et al. |
| 7,582,802 B2 | 9/2009 | Caers et al. |
| 7,863,487 B2 | 1/2011 | Eisenschmid et al. |
| 7,935,850 B2 | 5/2011 | Caers et al. |
| 8,404,903 B2 | 3/2013 | Cox et al. |
| 9,174,907 B2 | 11/2015 | Brammer et al. |
| 9,328,047 B2 | 5/2016 | Miller et al. |
| 9,676,685 B2 | 6/2017 | Watson et al. |
| 9,809,520 B2 | 11/2017 | Cheng et al. |
| 10,023,516 B2 | 7/2018 | Brammer et al. |
| 10,131,608 B2 | 11/2018 | Miller et al. |
| 2003/0018220 A1 | 1/2003 | Puckette et al. |
| 2005/0209469 A1 | 9/2005 | Shutt et al. |
| 2005/0229479 A1 | 10/2005 | Fernandes |
| 2006/0224000 A1 | 10/2006 | Papp et al. |
| 2007/0112220 A1 | 5/2007 | Caers et al. |
| 2007/0282132 A1 | 12/2007 | Beadle et al. |
| 2007/0282134 A1 | 12/2007 | Caers et al. |
| 2012/0172630 A1 | 7/2012 | Liu |
| 2014/0350307 A1 | 11/2014 | Eom et al. |
| 2015/0045586 A1 * | 2/2015 | Vijayakumari ....... C07C 29/141 568/451 |
| 2015/0307430 A1 | 10/2015 | Miller et al. |
| 2015/0376101 A1 | 12/2015 | Eisenschmid |

FOREIGN PATENT DOCUMENTS

| | | |
|---|---|---|
| DE | 102013219506 | 4/2014 |
| DE | 102013219508 | 4/2014 |
| EP | 0052999 | 6/1982 |
| FR | 2953828 | 6/2011 |
| GB | 1283774 | 8/1972 |
| WO | 88/08835 | 11/1988 |
| WO | 2001051441 | 7/2001 |
| WO | 2005028404 | 3/2005 |
| WO | 2011/115695 | 9/2011 |
| WO | 2015094781 | 6/2015 |

OTHER PUBLICATIONS

Tudor, Richard, et al., "Enhancement of Industrial Hydroformylation Processes by the Adoption of Rhodium-Based Catalyst: Part II", Platinum Metals Review, 2007, vol. 51, pp. 164-171.

Kokkinos, Nikolaos, et al., "Hydrogenation of a hydroformylated naphtha model (mixture of specific aldehydes) catalyzed by Ru/TPPTS complex in aqueous media", Applied Catalysis A: General, vol. 363, 2009, pp. 129-134.

Marchionna, et al., "High quality fuel components from C4 hydrocarbons", DGMK Conference, 2004, pp. 125-135, Munich.

PCT/US2017/017325, International Preliminary Report on Patentability dated Aug. 14, 2018.

PCT/US2017/017325, International Search Report and Written Opinion dated Apr. 20, 2017.

* cited by examiner

PROCESS FOR CONVERTING OLEFINS TO ALCOHOLS, ETHERS, OR COMBINATIONS THEREOF

FIELD

The present invention relates to the hydroformylation of olefin streams to make useful aldehyde intermediates and derivatives products. In particular, the present invention relates to the hydroformylation of an olefin containing stream wherein substantial amounts of alkane are present. More particularly, in some embodiments, the present invention relates to the hydroformylation of such streams to form oxygenates suitable for use as gasoline additives.

INTRODUCTION

Hydroformylation involves reacting at least one olefin with carbon monoxide and hydrogen using a transition metal catalyst. The product of the reaction is one or more aldehydes, and perhaps certain aldehyde derivatives depending upon the process. Derivatives of aldehydes include alcohols, acids, ethers, and esters.

Olefins that are used to produce aldehyde products are typically made by cracking petroleum or natural gas for feedstocks. Cracking is the cleavage of saturated carbon-carbon bonds with coincident removal of hydrogen to produce unsaturated olefins of varying molecular weight and can be accomplished catalytically or non-catalytically. The resulting stream comprises a mixture of both olefin(s) (alkenes) and saturated hydrocarbons (alkanes).

In general, the resulting mixed hydrocarbon stream is subjected to various refining processes that can separate the mixture based on boiling points and in practice, various "cuts" are taken that roughly correlate with the number of carbons (i.e., a "C2 cut" is a mixture of ethylene/ethane; a "C3 cut" is a mixture of propylene/propane; a "C4 cut" is a mixture of butenes/butanes). However, further separation of the alkene from the alkane is not trivial and may require many stages of separation and extreme operating conditions, particularly if a high purity olefin product is desired. Depending on the composition of the starting stream (i.e., C2 or C3 or C4 cut), the potential value of the high purity olefin contained within that stream may or may not justify the cost of further refining. Thus, in many refinery operations, different grades of olefin streams (commonly referred to and in order of increasing (low to high) purity as: "refinery grade", "chemical grade" and "polymer grade") are available and may be underutilized.

It would thus be desirable to convert these lower quality, lower value olefin/alkane streams into valuable products which are suitable for use on-site and increase the operational flexibility of the refinery.

In addition, neither ethylene/ethane or propylene/propane are liquids at ambient conditions such that expensive gas processing (e.g., compression), storage, burning these streams as a fuel source, or flaring would be required if pipelines or other facilities for further processing into valuable chemicals are not available at the refinery site.

Prior art, such as US Patent Publication No. 2005/0209469, has taught that for economic reasons, the raw material used for such industrial scale processes should have the highest available purity such as chemical grade propylene, which contains about 90-95 wt % propylene, with the majority of the balance being propane, with polymer grade polypropylene (95% or higher propylene) being even more preferred. As another example, DE-A-10035370 is concerned with an improved two reactor recycle hydroformylation system which reduces propylene losses. This recycle system is said to reduce propylene loss in the off gas. In the example in DE-A-10035370, polymer grade propylene which contains about 99.5 wt % propylene, the 0.5 wt % balance being propane, is used as the feedstock for low pressure, rhodium catalysed, hydroformylation.

U.S. Pat. No. 6,969,777 teaches to hydroformylate a crude olefin feed and then perform the olefin/alkane separation of the gaseous effluent after the hydroformylation reactor. This still requires an expensive distillation column which, for C2-C4 olefins, would require either high pressure or cryogenic cooling. Since the olefins are lowest boiling, they will be taken off the top of the column but any aldehyde in the vents will be lost out the bottom of the column with the alkanes (the aldehyde having a significantly higher boiling point than either the olefin or alkane). Such a system is particularly inefficient when the alkane content in the olefin feed stream is large.

Industrial hydroformylations are generally continuous processes which do not result in 100% conversion of the olefin. The selectivity to desired products is also not 100%, and a small portion of the olefin is hydrogenated to alkane. For example, the products of the hydroformylation of chemical grade propylene include the target butyraldehyde and butanol streams along with an off gas stream comprising unreacted propylene, propane, and unreacted carbon monoxide and hydrogen. In general, it is economically desirable to recycle the unreacted olefin, carbon monoxide and hydrogen in a hydroformylation process; however this becomes difficult if this recycle gas stream contains high levels of alkane, as the excess alkane may accumulate in the reaction system. In order to prevent alkane accumulation due to the recycling of gases, it is necessary to vent off some, if not all, of the alkane for use elsewhere (e.g., recycle to cracker, burn as fuel, flare). This alkane purge will invariably result in loss of olefin; thus, the general approach in hydroformylation processes is to avoid olefin feeds with high levels of alkanes.

In attempting to hydroformylate dilute, lower grade olefin feeds, degradation of catalyst and/or ligands is another concern. It would be desirable to have a process that converts a substantial portion of dilute, lower grade olefin feeds to a useful product without serious catalyst and/or ligand degradation.

Low purity olefin streams are found in many industrial processes but most commonly in petrochemical refining operations. These streams have some utility; in particular, C3 or C4 streams with significant alkene/alkane content are often used for alkylation to produce octane boosting alkylates for the refinery's gasoline pool (e.g., reacting propylene with isobutene to produce the alkylate 2,4-dimethylpentane). The C4 streams are preferred in such an application; thus, finding an alternative use for the C3 stream would enable more of the C4 to be utilized in the alkylation unit and improve operation of the refinery.

In short, there remains a need for uses of dilute, lower grade olefin streams, such as C3 or C4 streams in a petrochemical refining operation, that are economically viable and that provide useful and value added products.

SUMMARY

The present invention advantageously provides processes that convert a substantial portion of dilute, lower grade olefin within a high alkane content stream to a useful product. In particular, the present invention advantageously converts a dilute, lower grade olefin stream to highly branched oxygenates that can be used in an economically feasible manner in high yield. Surprisingly, the present invention can advantageously convert such streams to value-added oxygenates without serious catalyst and/or ligand degradation. For example, some embodiments of the present invention utilize a highly active hydroformylation catalyst that is reactive enough to convert dilute olefin streams to aldehydes at high conversion, without significant catalyst or ligand degradation, yielding a highly branched aldehyde product that can be readily hydrogenated to a fuel-grade alcohol mixture without substantial refining.

In one aspect, the present invention provides a process for converting olefins to alcohols, ethers, or combinations thereof that are suitable for use as a gasoline additive, the process comprising (a) receiving a feed stream, wherein the feed stream comprises one or more olefins having 2 to 5 carbon atoms in an amount of up to 80% by weight based on the weight of the feed stream; (b) hydroformylating the feed stream in the presence of a catalyst to convert at least 80% of the olefins from the feed stream to oxygenates; (c) separating a product stream from step (b) into an oxygenate stream and a stream comprising unreacted olefins, inerts, the catalyst, and the remaining oxygenates; and (d) treating the oxygenate stream to convert a plurality of the oxygenates into at least one of an alcohol, an ether, or combinations thereof having at least 3 carbon atoms, wherein at least 25 weight percent of the alcohols and ethers having at least 3 carbon atoms are branched based on the total weight of the alcohols and ethers having at least 3 carbon atoms, and wherein the alcohols, ethers, or combination thereof is suitable for use as a gasoline additive.

In one aspect, the present invention provides a process for converting olefins to alcohols, ethers, or combinations thereof that are suitable for use as a gasoline additive, the process comprising (a) receiving a feed stream, wherein the feed stream comprises one or more olefins having 2 to 5 carbon atoms in an amount of up to 80% by weight based on the weight of the feed stream, and wherein propylene comprises at least 50% by weight of the feed stream; (b) hydroformylating the feed stream in the presence of a catalyst to convert at least 80% of the olefins from the feed stream to oxygenates; (c) separating a product stream from step (b) into an oxygenate stream and a stream comprising unreacted olefins, inerts, the catalyst, and the remaining oxygenates; and (d) treating the oxygenate stream to convert a plurality of the oxygenates into at least one of an alcohol, an ether, or combinations thereof having at least 3 carbon atoms, wherein at least 25 weight percent of the alcohols and ethers having at least 3 carbon atoms are branched based on the total weight of the alcohols and ethers having at least 3 carbon atoms, and wherein the alcohols, ethers, or combination thereof is suitable for use as a gasoline additive.

In one aspect, the present invention provides a process for converting olefins to alcohols, ethers, or combinations thereof that are suitable for use as a gasoline additive, the process comprising (a) receiving a feed stream, wherein the feed stream comprises one or more olefins having 2 to 5 carbon atoms in an amount of up to 80% by weight based on the weight of the feed stream, and wherein ethylene comprises at least 50% by weight of the feed stream; (b) hydroformylating the feed stream in the presence of a catalyst to convert at least 80% of the olefins from the feed stream to oxygenates; (c) separating a product stream from step (b) into an oxygenate stream and a stream comprising unreacted olefins, inerts, the catalyst, and the remaining oxygenates; and (d) treating the oxygenate stream to convert a plurality of the oxygenates into at least one of an alcohol, an ether, or combinations thereof having at least 3 carbon atoms and wherein the alcohols, ethers, or combination thereof is suitable for use as a gasoline additive.

In some embodiments, at least 90% of the olefins in the feed stream are converted to oxygenates in the hydroformylation of step (b). At least 95% of the olefins in the feed stream are converted to oxygenates in the hydroformylation of step (b) in some embodiments.

These and other embodiments are discussed in more detailed in the Detailed Description.

DETAILED DESCRIPTION

Figure 1A:
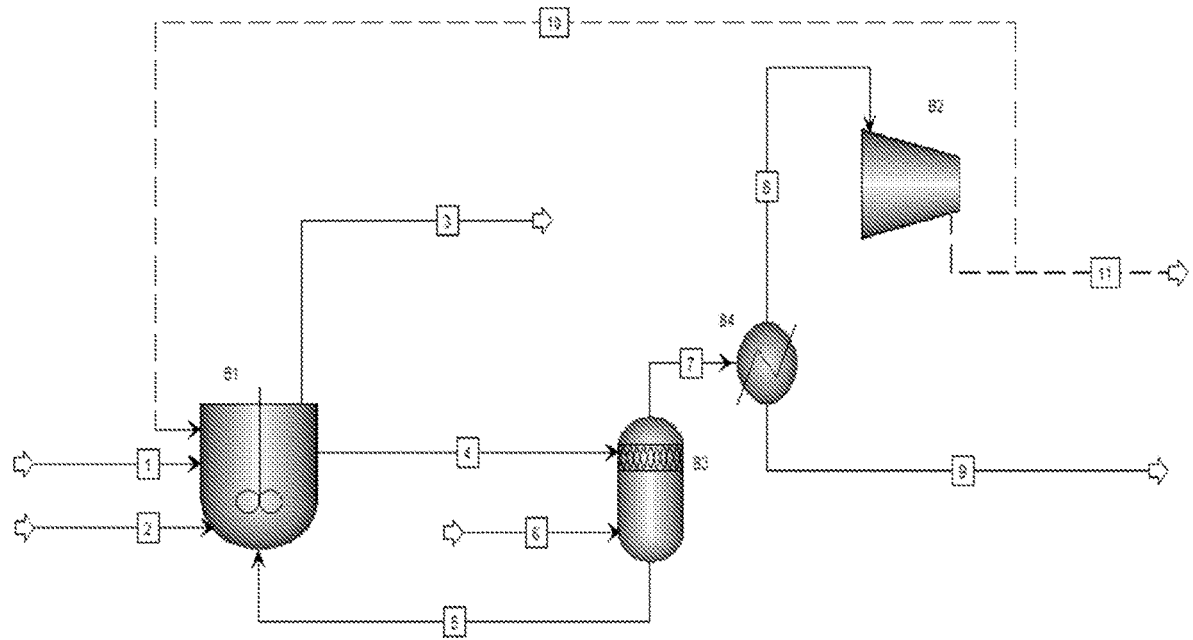
FIGS. 1A and 1B represent a flow sheet illustrating a system for performing a process according to one embodiment of the present invention.

In general, the present invention is concerned with a method comprising hydroformylating an olefin stream of moderate to high alkane content and further processing at least a portion of the hydroformylation products to produce a gasoline additive. A particular advantage of some embodiments, in addition to other advantages discussed herein, is the conversion of a gaseous stream (olefin, syngas) to a liquid fuel stream (alcohol, gasoline/alcohol blend) suitable for transportation by conventional trucks and railcars as opposed to high pressure gas or liquefied gas transportation containers or gas pipelines.

All references to the Periodic Table of the Elements and the various groups therein are to the version published in the CRC Handbook of Chemistry and Physics, 72nd Ed. (1991-1992) CRC Press, at page I-11.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means parts per million by weight.

As used herein, the term "N/I ratio" or "N/I" refers to the ratio of normal aldehydes (N) to branched isomers (I) wherein a branch (methyl group) occurs next to (alpha to) the aldehyde moiety. This terminology generally refers to which carbon of a terminal olefin the CO moiety binds to compared to the hydrogen moiety and not related to any branching present in the olefin. For example, propylene will generate n-butyraldehyde (N isomer) and isobutyraldehyde (I isomer).

By "tonnes" is meant metric tonnes, so 2 tonnes per hour is 2000 kg per hour—in other words, an industrial scale process. Of course, references to feed rate is to that applicable during normal operation of the process. Shut down of the process for maintenance and other reasons may occur without impacting the scope of the invention.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces) and (g) organophosphorous ligand decomposition products such as the hydrolysis products and/or the corresponding oxide(s). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid that has undergone a catalyst treatment step (e.g., treatment with an aqueous buffer, treatment with an aqueous solution of alkanolamine(s), such as described in PCT Publication No. WO2015/153070, etc.), (g) a treated fluid returned to a reaction zone or separation zone, (h) a fluid in an external cooler, and (i) ligand decomposition products and their salts.

Embodiments of the present invention relate to processes for converting olefins to alcohols, ethers, or combinations thereof that are suitable for use as a gasoline additive. The term "gasoline" is used herein in a manner consistent with the understanding of those of ordinary skill in the art and includes, for example, motor fuels.

Governmental regulations in the United States require that motor fuels such as gasoline be formulated in a manner to avoid production of certain noxious waste by-products discharged to the atmosphere when the fuel is burned in an engine. These regulations are directed toward the reduction of olefins and aromatics, and in order to implement such goals, require the presence of oxygen. Addition of oxygenates to gasoline is intended to reduce hydrocarbon and carbon monoxide exhaust emissions to a level which meets presently mandated emission standards.

Alcohols have long been added to motor fuels such as gasoline to increase the octane rating of the fuel. Ethanol has properties which limit its use as a motor fuel additive, particularly if employed at levels which are effective in reducing unburned hydrocarbon and carbon monoxide combustion by-products. Ethanol, which has been dehydrated to an extent that the cost of the product is low enough to permit economic use of the alcohol as a gasoline additive, still contains an amount of water that causes the alcohol to be immiscible in the fuel. As a result, the ethanol additive tends to separate from the hydrocarbon fuel under certain ambient temperature conditions. Furthermore, gasoline while stored can accumulate additional quantities of water from the atmosphere. This exposure of the gasoline to additional water can trigger phase separation of the alcohol from the fuel.

A co-solvent can be added to prevent phase separation of the C1 and C2 alcohols from the fuel. Tertiary butyl alcohol (TBA) is an example of a co-solvent that has been used with C1 and C2 additives for motor fuels.

When alcohols, ethers, or combinations thereof from processes disclosed herein are to be added to gasoline, it should be understood that the alcohols, ethers, or combinations can be added with other motor fuel additives, prior to the addition of other motor fuel additives, and/or after the addition of other motor fuel additives.

Current oxygenates used as motor fuel additives include methyl tertiary butyl ether (MTBE), ethyl tertiary butyl ether (ETBE), and tertiary amyl methyl ether (TAME). These products proved to be expensive and required importation of methanol for production of MTBE and TAME, or ethanol for preparation of ETBE. Methanol or ethanol are not products which are conventionally produced in refinery processes, thus increasing the cost of the additive.

According to some embodiments, the present invention provides processes for using a low-purity olefin stream with a rhodium hydroformylation catalyst to form a hydroformylated product and then hydrogenating the crude aldehyde product to an alcohol, ether, or combination thereof suitable to being used as a gasoline additive to increase the oxygenate content. In certain embodiments, the use of highly active, low N/I hydroformylation conditions (including, for example, utilization of a ligand which is selective to low N/I aldehyde ratios) to generate highly branched alcohols from the low grade olefin streams would produce valuable and highly effective fuel additives.

According to one embodiment, a process of the present invention for converting olefins to alcohols, ethers, or combinations thereof that are suitable for use as a gasoline additive comprises (a) receiving a feed stream, wherein the feed stream comprises one or more olefins having 2 to 5 carbon atoms in an amount of up to 80% by weight based on the weight of the feed stream; (b) hydroformylating the feed stream in the presence of a catalyst to convert at least 80% of the olefins from the feed stream to oxygenates; (c) separating a product stream from step (b) into an oxygenate stream and a stream comprising unreacted olefins, inerts, the catalyst, and the remaining oxygenates; and (d) treating the oxygenate stream to convert a plurality of the oxygenates into at least one of an alcohol, an ether, or combinations thereof having at least 3 carbon atoms, wherein at least 25 weight percent of the alcohols and ethers having at least 3 carbon atoms are branched based on the total weight of the alcohols and ethers having at least 3 carbon atoms, and wherein the alcohols, ethers, or combination thereof is suitable for use as a gasoline additive.

In some embodiments, at least 90% of the olefins in the feed stream are converted to oxygenates in the hydroformylation of step (b). At least 95% of the olefins in the feed stream are converted to oxygenates in the hydroformylation of step (b) in some embodiments.

In some embodiments, the feed stream comprises at least 50% by weight propylene based on the total weight of the feed stream. The feed stream comprises at least 60% by weight propylene based on the total weight of the feed stream in some embodiments. The feed stream, in some embodiments, comprises at least 70% by weight propylene based on the total weight of the feed stream.

In some embodiments, the feed stream comprises at least 50% by weight ethylene based on the total weight of the feed stream. The feed stream comprises at least 60% by weight ethylene based on the total weight of the feed stream in some embodiments. The feed stream, in some embodiments, comprises at least 70% by weight ethylene based on the total weight of the feed stream.

In some embodiments, the feed stream comprises at least 50% by weight butene based on the total weight of the feed stream. The feed stream comprises at least 60% by weight butene based on the total weight of the feed stream in some embodiments. The feed stream, in some embodiments, comprises at least 70% by weight butene based on the total weight of the feed stream.

In some embodiments, the feed stream comprises at least 50 weight percent olefins (including mixtures of olefins) having 2 to 5 carbon atoms based on the weight of the feed stream. The feed stream, in some embodiments, comprises at least 55 weight percent olefins having 2 to 5 carbon atoms based on the weight of the feed stream. In some embodiments, ethylene, propylene, and/or butene comprise at least 60% of the feed stream based on the total weight of the feed stream.

In some embodiments, the feed stream further comprises alkanes, and other inerts found in gaseous olefin streams. In some embodiments, the feed stream comprises at least 15 weight percent alkanes based on the weight of the feed stream. The feed stream, in some embodiments, comprises at least 20 weight percent alkanes based on the weight of the feed stream. In some embodiments, the feed stream comprises at least 30 weight percent alkanes based on the weight of the feed stream. The feed stream comprises at least 35 weight percent alkanes based on the weight of the feed stream in some embodiments. The feed stream, in some embodiments, comprises up to 50 weight percent alkanes based on the weight of the feed stream. The feed stream comprises up to 45 weight percent alkanes based on the weight of the feed stream in some embodiments. In some embodiments, the feed stream comprises up to 40 weight percent alkanes based on the weight of the feed stream.

The feed stream may or may not contain polyunsaturated impurities, such as methylacetylene, propadiene, butadiene, and 1- and 2-butynes at concentrations of each ranging from 0 to up to 1000 ppmw or more. Such impurities may or may not need to be removed from the feedstock before hydroformylation. If such impurities do need to be removed, they can be removed by processes well-known in the art such as reaction with hydrogen to form alkanes as disclosed, for example, in PCT Publication No. WO2014/209736A1.

In some embodiments, hydroformylating the feed stream in step (b) converts at least 80% of the olefins from the feed stream to oxygenates. Hydroformylating the feed stream in step (b), in some embodiments, converts at least 90% of the olefins from the feed stream to oxygenates. In some embodiments, hydroformylating the feed stream in step (b) converts at least 95% of the olefins from the feed stream to oxygenates. Additional details regarding the hydroformylation that can be carried out in step (b) are set forth below. For example, in some embodiments, the hydroformylation in step (b) can be carried out in the presence of an amine. As another example, certain catalysts are particularly useful for hydroformylation according to some embodiments of the present invention. For example, rhodium-based catalysts that are particularly active (e.g., having a reaction rate of greater than greater than 0.5 turnovers/second on a rhodium-atom basis) can be used in some embodiments of the present invention.

In some embodiments, the separation step (c) can be performed using a stripping gas vaporizer as discussed in more detail below. For example, in some embodiments where the feed gas comprises inerts or alkanes, such inerts or alkanes or unreacted olefins or syngas from the feed stream can be used to facilitate separation. In some embodiments, the stream comprising unreacted olefins, inerts, catalyst, and the remaining oxygenates from step (c) can be treated with an aqueous buffer to remove undesired, acidic ligand byproducts from the catalyst solution and improve/maintain ligand and catalyst stability.

As discussed in more detail below, the oxygenate stream in step (c) comprises an aldehyde. Examples of such aldehydes are discussed below. In some embodiments, at least 80 weight percent of the oxygenates in step (c) are formed by the hydroformylation in step (b).

Oxygenates in the oxygenate stream of step (c), such as aldehydes, can be treated to convert a plurality of the oxygenates into alcohols, ethers, or combinations thereof, in some embodiments. For example, in some embodiments, treating the oxygenate stream according to step (d) comprises hydrogenation of the oxygenate into an alcohol. As another example, in some embodiments, the oxygenates comprise an isobutyraldehyde and wherein treating the oxygenate stream comprises hydrogenation of the isobutyraldehyde into isobutyl alcohol or diisobutyl ether. In some embodiments, at least a portion of the oxygenates from the oxygenate stream in step (c) are converted into esters. One example of such an ester is butyl butyrate.

In some embodiments, treating the oxygenate stream in step (d) further comprises removing water. Water may be removed, in some embodiments, particularly when the stream comprising alcohols and ethers is to be provided to gasoline.

In some embodiments, processes of the present invention comprise removing at least some of the alcohols and ethers after step (d). This process can be used to increase the branched alcohol component by removing linear alcohols, for example. Alcohols and/or ethers provided by processes of the present invention can be added to gasoline, in some embodiments. For example, the linear alcohols removed can be provided for other uses, while the branched alcohols and/or ethers can be provided to gasoline.

In some embodiments, at least 90% of the alcohols from step (d) comprise alcohols having 3 to 6 carbon atoms.

As noted above, the use of highly active, low N/I hydroformylation conditions to generate highly branched alcohols from the low grade olefin streams can produce valuable and highly effective fuel additives. At least 25% of the alcohols and ethers having at least 3 carbon atoms produced in some embodiments are branched based on the total weight of the alcohols and ethers having at least 3 carbon atoms. In some embodiments, at least 40% of the alcohols and ethers having at least 3 carbon atoms are branched based on the total weight of the alcohols and ethers having at least 3 carbon atoms. The extent of branching is readily determined by well known, conventional gas chromatography (GC). As used herein, the weight composition of alcohols is determined by conventional GC analysis of a sample using conventional GC columns, calibrated with alcohols standards to determine retention times and detector response factors. Appropriate summing of linear and branched alcohol weight percents can be performed to give the composition and extent of branching.

For the purposes of this invention, "n-" or "linear" alcohols are those that have no branching in the structure and thus only contain one —$CH_3$ moiety. Linear alcohols include, for example, n-propanol, n-butanol, and n-pentanol. "Branched" alcohols have a branch in the structure whether next to or down the alkyl chain from the alcohol. Examples of branched alcohols include isobutanol, 2-methylbutanol, and 2,2-dimethylpropanol. If the branch is specifically located next to the alcohol or aldehyde moiety, the material will be termed "iso" such as in isobutanol.

Turning now to the hydroformylation step according to processes of the present invention, in addition to the olefins in the feed stream, other reactants include hydrogen and carbon monoxide which are reacted with the olefins in the presence of a catalyst. Hydrogen and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO molar ratio for chemical production is between 3:1 and 1:3 and usually is targeted to be between about 1:2 and 2:1 for most hydroformylation applications.

The substituted or unsubstituted olefinic unsaturated reactants that may be employed in the hydroformylation process include both optically active (prochiral and chiral) and non-optically active (achiral) olefinic unsaturated compounds containing from 2 to 5, preferably 3 to 4, carbon atoms. These compounds are described in detail in U.S. Pat. No. 7,863,487. Such olefinic unsaturated compounds can be terminally or internally unsaturated and be of straight-chain, branched chain or cyclic structures, as well as olefin mixtures.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,830 and 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri-organophosphorus ligands, and are preferably non-chelating ligands. Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

The preferred organophosphorus ligands useful in this invention generate highly reactive catalysts. These ligands are preferably triarylphosphines, diarylalkylphosphines, dialkylarylphosphines, triorganophosphites, diorganophosphites, and the like. In general, the ligands are not polydentate unless the separation between phosphorous atoms is either greater than 10 atoms or the link prevents the phosphorous atoms to chelate to a single metal atom.

The resulting organophosphorous ligand-metal catalyst should have a reactivity of greater than 0.5 turnovers/second on a rhodium-atom basis. In some embodiments, the resulting organophosphorous ligand-metal catalyst has a reactivity of greater than 1 turnovers/second on a rhodium-atom basis.

Among the organophosphorous ligands that may serve as the ligand of the metal-organophosphorous ligand complex catalyst are organophosphites such as monoorganophosphite, diorganophosphite, and triorganophosphite compounds. Such organophosphorous ligands and methods for their preparation are well known in the art.

Representative monoorganophosphites may include those having the formula:

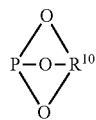

(I)

wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane and the like, or trivalent cycloalkylene radicals such as those derived from 1,3,5-trihydroxycyclohexane and the like. Such monoorganophosphites may be found described in greater detail, for example, in U.S. Pat. No. 4,567,306.

Representative diorganophosphites may include those having the formula:

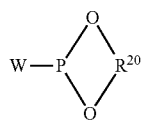

(II)

wherein $R^{20}$ represents a substituted or unsubstituted divalent hydrocarbon radical containing from 4 to 40 carbon atoms or greater and W represents fluoride or a substituted or unsubstituted alkoxy or aryloxy moiety containing from 1 to 18 carbon atoms or greater.

Representative substituted and unsubstituted monovalent hydrocarbon radicals represented by W in the above Formula (II) include alkoxy, aryloxy, or fluoride radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-$NR^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302 and the like. Illustrative divalent aromatic radicals include, for example, arylene, biarylene, arylene-alkylene, arylene-alkylene-arylene, arylene-oxy-arylene, arylene-$NR^{24}$-arylene wherein $R^{24}$ is as defined above, arylene-S-arylene, arylene-S-alkylene and the like. More preferably $R^{20}$ is a divalent aromatic radical such as disclosed more fully, for example, in U.S. Pat. Nos. 4,599,206, 4,717,775, 4,835,299, and the like. An example of a preferred diorganophosphite is 4,8-bis(1,1-dimethylethyl)-6-[2-(1,1-dimethylethyl)-4-methoxyphenoxy]-2,10-dimethoxy-dibenzo[d,f][1,3,2]dioxaphosphepin.

Representative of a more preferred class of diorganophosphites are those of the formula:

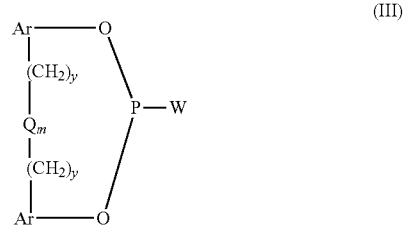

(III)

wherein W is as defined above, each Ar is the same or different and represents a substituted or unsubstituted aryl radical, each y is the same or different and is a value of 0 or 1, Q represents a divalent bridging group selected from —C($R^{33}$)$_2$—, —O—, —S—, —$NR^{24}$—, Si($R^{35}$)$_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

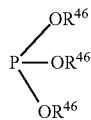

(IV)

wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, and the like, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, 2,6-di-t-butyl-4-methylphenyl-1,1'-biphenyl-2,2'diylphosphite, tris(3,6-di-t-butyl-2-naphthyl)phosphite, bis(3,6,8-tri-t-butyl-2-naphthyl)phenylphosphite, and bis(3,6,8-tri-t-butyl-2-naphthyl)(4-sulfonylphenyl)phosphite, and the like. Such triorganophosphites are described in greater detail, for example, in U.S. Pat. Nos. 3,527,809 and 4,717,775.

Any of the $R^{10}$, $R^{20}$, W, X, Q and Ar radicals of such organophosphites of Formulas (I) to (IV) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —Si($R^{35}$)$_3$; amino radicals such as —N($R^{15}$)$_2$; phosphine radicals such as -aryl-P($R^{15}$)$_2$; acyl radicals such as —C(O)$R^{15}$ acyloxy radicals such as —OC(O)$R^{15}$; amido radicals such as —CON($R^{15}$)$_2$ and —N($R^{15}$)COR$^{15}$; sulfonyl radicals such as —SO$_2$R$^{15}$, alkoxy radicals such as —OR'; sulfinyl radicals such as —SOR$^{15}$, phosphonyl radicals such as —P(O)(R$^{15}$)$_2$, as well as halo, nitro, cyano, trifluoromethyl, hydroxy radicals and the like, wherein each $R^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N($R^{15}$)$_2$ each $R^{15}$ taken together can also represent a divalent bridging group that forms a heterocyclic radical with the nitrogen atom, and in amido substituents such as —C(O)N($R^{15}$)$_2$ and —N($R^{15}$)COR$^{15}$ each $R^{15}$ bonded to N can also be hydrogen. It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neopentyl, n-hexyl, amyl, sec-amyl, t-amyl, iso-octyl, decyl, octadecyl, and the like; aryl radicals such as phenyl, naphthyl, and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy, —OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; amino radicals such as —NH$_2$, —N(CH$_3$)$_2$, —NHCH$_3$, —NH(C$_2$H$_5$), and the like; arylphosphine radicals such as —P(C$_6$H$_5$)$_2$, and the like; acyl radicals such as —C(O)CH$_3$, —C(O)C$_2$H$_5$, —C(O)C$_6$H$_5$, and the like; carbonyloxy radicals such as —C(O)OCH$_3$, and the like; oxycarbonyl radicals such as —O(CO)C$_6$H$_5$ and the like; amido radicals such as —CONH$_2$, —CON(CH$_3$)$_2$, —NHC(O)CH$_3$, and the like; sulfonyl radicals such as —S(O)$_2$C$_2$H$_5$ and the like; sulfinyl radicals such as —S(O)CH$_3$ and the like; sulfidyl radicals such as —SCH$_3$, —SC$_2$H$_5$, —SC$_6$H$_5$, and the like; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), —P(O)(H)(C$_6$H$_5$), and the like.

Specific illustrative examples of such organophosphite ligands include the following: 2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, and [1,1'-biphenyl]-2,2'-diyl tetrakis[2-(1,1-dimethylethyl)-4-methoxyphenyl]ester of phosphorous acid.

The preferred triorganophosphine ligand employable in the process of this disclosure comprises any organic compound comprising one phosphorus atom covalently bonded to three alkyl, cycloalkyl, aryl or arylalkyl radicals, or combinations thereof. A mixture of triorganolphosphine ligands may also be employed. Representative organomonophosphines include those having the formula:

(V)

wherein each $R^{29}$, $R^{30}$ and $R^{31}$ may be the same or different and represent a substituted or unsubstituted alkyl, cycloalkyl or aryl radical containing from 4 to 40 carbon atoms or greater. Such triorganophosphines may be found described in greater detail, for example, in U.S. Pat. Nos. 3,527,809 and 4,283,562 and sulphonated derivatives described in U.S. Pat. No. 4,248,802, the disclosure of which is incorporated herein by reference. Illustrative triarylphosphine ligands are triphenylphosphine, trinaphthylphosphine, tritolylphosphine, tri(p-biphenyl)phosphine, tri(p-methoxyphenyl)phosphine, tri(m-chlorophenyl)-phosphine, p-N,N-dimethylaminophenyl bis-phenyl phosphine, and the like. Dicyclohexylphenylphosphine and cyclohexyldiphenylphosphine are preferred mixed-alkylarylphosphines. Triphenyl phosphine, i.e. the compound of Formula II wherein each $R^{29}$, $R^{30}$ and $R^{31}$ is phenyl, is an example of a preferred organomonophosphine ligand. As pointed out previously, the reaction is effected in a liquid body containing excess, free triorganophosphine.

As a desired consequence of employing highly active catalysts, the observed aldehyde isomer ratio (N/I) for C3 and higher olefins will tend to be low. Since the octane rating is higher for branched oxygenates, this is a fortuitous outcome of reacting lower reactivity olefin feeds with more reactive catalysts. In particular, internal olefins such as cis/trans 2-butene will generate branched oxygenate unless isomerizing of the olefin occurs prior to hydroformylation. The ligands described above will not generate high (>15) N/I ratios and thus are preferred to generate highly branched oxygenates to process into highly branched gasoline additives. For example, 2-butene will predominately produce 2-methylbutyraldehyde which, when hydrogenated, will generate 2-methylbutanol which contains a methyl branch.

Branched olefins such as isobutene will produce essentially entirely branched oxygenates and thus are a preferred olefin component. For example, isobutene will generate predominately 3-methylbutyraldehyde which, upon hydrogenation, will give 3-butanol. In contrast to other technologies employing isobutylene, hydroformylation will not generate significant amounts of 2,2-dimethylpropionaldehyde or any species which contains a quaternary carbon (unless present in the olefin). Materials with tertiary and especially quaternary carbons are known to have low biodegradability. Examples of moieties having tertiary and quaternary carbons which are used as gasoline additives include MTBE and t-butanol. Some embodiments of the present invention advantageously avoid producing and using such materials. In some embodiments, a process of the present invention provides an oxygenate stream comprising less than 1 weight percent quaternary carbons.

The preferred catalyst of this invention comprises rhodium complexed with carbon monoxide and a triarylphosphite ligand. The most desirable catalyst is free of metal-bound halogens such as chlorine, and contains hydrogen, carbon monoxide and triaryl phosphite complexed with rhodium metal to produce a catalyst soluble in the aforementioned liquid body and stable under the conditions of the reaction.

Rhodium is preferably introduced into the liquid body as a preformed catalyst, e.g., a stable crystalline solid, rhodium dicarbonyl acetylacetonate (Rh (acac)). The rhodium can be introduced to the liquid body as a precursor form which is converted in situ into the catalyst. Examples of such precursor form are rhodium carbonyl triphenylphosphine acetylacetonate, $Rh_2O_3$, $Rh_4(CO)_{12}$, $Rh_6(CO)_{16}$, and rhodium hydridocarbonyl-tris(triphenyl phosphine), $RhH(CO)(PPh_3)_3$. Both the catalyst compounds which will provide active species in the reaction medium and their preparation are known by the art, see Brown et al., *Journal of the Chemical Society*, 1970, pp. 2753-2764.

In general the optimum catalyst concentration depends on the concentration of the alpha-olefin, such as propylene. For example, the higher the propylene concentration the lower usually will be the catalyst concentration that can be used to achieve a given conversion rate to aldehyde products in a given size of reactor. The prior art taught that partial pressures and concentration are related, the use of higher propylene partial pressure leads to an increased proportion of propylene in the "off gas" (vent) from the liquid body. Since it may be necessary to purge part of the gas stream from the product recovery zone before recycle to the liquid body in order to remove a portion of the propane which may be present, the higher the propylene content of the "off gas" is, the more propylene that will be lost in the propane purge stream. Thus it is necessary to balance the economic value of the propylene lost in the propane purge stream against the capital savings associated with lower catalyst concentration. In the present invention, it is recognized that the higher vent losses will result as a function of the more dilute feed but since the feed has lower value than those considered by the prior art, the economic penalty of concern for them is mitigated in the present case. Additionally, the higher activity catalysts employed herein reduce the losses of unconverted olefin in the vents while simultaneously producing higher proportions of branched oxygenates which are more valued in the gasoline additive application.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1200 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The significance of free ligand is taught in U.S. Pat. No. 3,527,809, GB 1,338,225, and Brown et al., supra., pages 2759 and 2761. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 80 moles of organophosphorous ligand per mole of metal present in the reaction medium. More preferably, for arylphosphines, from 3 to 70 moles of arylphosphine ligand are employed per mole of metal. Said amounts of organophosphorous ligand are the sum of both the amount of organophosphorous ligand that is bound (complexed) to the metal present and the amount of free organophosphorous ligand present. If desired, additional organophosphorous ligand can be supplied to the reaction medium of the hydroformylation process at any time and in any suitable manner, e.g. to maintain a predetermined level of free ligand in the reaction medium.

When an organophosphite is used, it is present in the range of about 0.05 percent to about 30 percent by weight, based on the weight of the total reaction mixture, and preferably in an amount sufficient to provide at least 3 moles, preferably at least 5 moles, and most preferably at least 10 moles of free triarylphosphite per mole of rhodium.

In general, lower excess organophosphorous ligand in solution gives lower N/I ratios and often more reactive catalysts. Extremely low excess ligand risks rhodium loss and other side reactions thus care is kept to insure at least 3 moles and preferably more than 5 moles of free organophosphorous ligand is present in the reaction fluid.

Hydroformylation processes, and conditions for their operation, are generally well known. The hydroformylation products may be asymmetric or non-asymmetric, the preferred products being non-asymmetric, and may be conducted in any batch, continuous or semi-continuous fashion and may involve any catalyst liquid and/or gas recycle operation desired.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. Nos. 5,430,194 and 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction fluid includes any fluid derived from any corresponding hydroformylation process that contains at least some amount of four different main ingredients or components, i.e., the aldehyde product, a metal-organophosphorous ligand complex catalyst, free organophosphorous ligand and a solvent for said catalyst and said free ligand. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, and in situ formed by-products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process may include any suitable type hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominantly by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1. In general, the hydroformylation process may be conducted at any operable reaction temperature. Advantageously, the hydroformylation process is conducted at a reaction temperature from −25° C. to 200° C., preferably from 50° C. to 120° C.

The hydroformylation process may be carried out using one or more suitable reactors such as, for example, a fixed bed reactor, a fluid bed reactor, a continuous stirred tank reactor (CSTR) or a slurry reactor. The optimum size and shape of the reactor will depend on the type of reactor used. The reaction zone employed may be a single vessel or may comprise two or more discrete vessels. The separation zone employed may be a single vessel or may comprise two or more discrete vessels. The reaction zone(s) and separation zone(s) employed herein may exist in the same vessel or in different vessels. For example, reactive separation techniques such as reactive distillation, and reactive membrane separation may occur in the reaction zone(s).

The hydroformylation process can be conducted with recycle of unconsumed starting materials if desired. The reaction can be conducted in a single reaction zone or in a plurality of reaction zones, and in series or in parallel. The reaction steps may be effected by the incremental addition of one of the starting materials to the other. Also, the reaction steps can be combined by the joint addition of the starting materials. The starting materials may be added to each or all of the reaction zones in series. When complete conversion is not desired or not obtainable, the starting materials can be separated from the product, for example by distillation, and the starting materials then recycled back into the reaction zone or concentrated by distillation prior to being recycled. In practice, with dilute feeds it is preferred that the operation be done on a single pass operation with the unreacted olefin and alkanes vented to the fuel header, used for syngas generation, or flared. In some embodiments, the unreacted olefins and alkanes can be used as refinery feedstock. When returned to a refinery, the unreacted alkanes can be used, for example, to enhance or balance the refinery's operation.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation process useful in this invention may be carried out in a multistaged reactor such as described, for example, in U.S. Pat. No. 5,728,893. Such multistaged reactors can be designed with internal, physical barriers that create more than one theoretical reactive stage per vessel.

It is generally preferred to carry out the hydroformylation process in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment, the aldehyde product mixtures may be separated from the other components of the crude reaction mixtures in which the aldehyde mixtures are produced by any suitable method such as, for example, solvent extraction, crystallization, distillation, vaporization, wiped film evaporation, falling film evaporation, phase separation, filtration, or any combination thereof. It may be desired to remove the aldehyde products from the crude reaction mixture as they are formed through the use of trapping agents as described in WO 88/08835. One method for separating the aldehyde mixtures from the other components of the crude reaction mixtures is by membrane separation, which is described, for example in U.S. Pat. Nos. 5,430,194 and 5,681,473.

As indicated above, desired aldehydes may be recovered from the reaction mixtures. For example, the recovery techniques disclosed in U.S. Pat. Nos. 4,148,830 and 4,247, 486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g. $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g. vaporizer/separator, wherein the desired aldehyde product is distilled. In general, distillation pressures ranging from vacuum pressures on up to total gas pressure of 340 kPa should be sufficient for most purposes.

U.S. Pat. No. 6,100,432 and PCT Publication WO2010/003073 teach the advantages of employing a stripping gas vaporizer to reduce the temperature needed to effect distillation of the product from the catalyst solution. In particular, these references focus on higher molecular weight aldehydes and the use of unreacted olefins and syngas as the stripping gas. The presence of high levels of alkanes in the feeds of the present invention has been found to be useful in reducing the temperature of the vaporizer by employing the contained alkanes as a stripping gas. The advantage of the high levels of alkanes to be used as the stripping gas is not believed to have been recognized by the prior art. In some cases, a recycle blower may not be necessary as the contained alkane may be sufficient to perform the stripping duty and little, if any, recycle would be needed.

The importance of the lower temperature in the vaporizer is increased due to the low concentration of reactants (olefin, syngas) typically present under these harsh conditions. In the absence of care and consideration for the catalyst, rhodium loss (usually as colloidal or insoluble metal) in the vaporizer may be observed with substantial activity loss. This loss of rhodium and/or catalytic activity is usually accompanied by color changes, loss of rhodium accountability by atomic absorption analysis of catalyst solutions, and conversion losses (often observed by increases in olefin partial pressures, less vaporized product, or by GC analysis of the headspace).

It has been found that the presence of one or more of the reactants helps stabilize the catalyst under the harsh vaporizer conditions. For example, phosphine-based catalysts tend to become unstable in the absence of olefin, and phosphite-based catalysts become vulnerable to degradation in the absence of carbon monoxide. The addition of syngas to stripping gas for a vaporizer to stabilize phosphite-based catalysts is taught in PCT Application PCT/US15/061332.

Thus, having fresh or unreacted syngas in the stripping gas feed to the vaporizer can be used to further stabilize phosphite-based catalysts. Likewise, a significant amount of unreacted olefin in the stripping gas fed to the vaporizer may help mitigate rhodium catalyst deactivation observed with phosphine-based catalysts. If phosphine-based rhodium catalyst is employed, it is important not to attempt to achieve 100% conversion of the olefin to avoid catalyst deactivation (see, e.g., U.S. Pat. No. 5,728,893).

An additional advantage can be found by using the hydroformylation reactor vents (particularly the last reaction zone in series) as one of the sources of stripping gas. Generally this vent is used to purge inerts and excess syngas or unreacted olefin from the system. Similarly, knockout pot vents and/or intermediate pressure let-down vessels vents can be used. This has the advantage of maintaining either syngas or unreacted olefin to assist in catalyst stability in the harsh vaporizer conditions. In particular, these vents are already at high pressure and temperature and are rich in aldehyde (thus helping mitigate evaporative losses).

Illustrative non-optically active aldehyde products include e.g., propionaldehyde, n-butyraldehyde, isobutyraldehyde, n-valeraldehyde, 2-methyl 1-butyraldehyde, 3-methylbutyraldehyde, hexanal, and hydroxyhexanal. Any polyunsaturates in the feeds will generate dialdehydes such as butane-1,4-dialdehyde, pentane-1,5-dialdehyde, 2-methyl)butane-1,4-(dialdehyde, (2-methyl)pentane-1,5-dialdehyde and pentane-1,6-dialdehyde.

The hydroformylation conditions employed for these dilute olefin streams are often more harsh compared to purified streams of the prior art. These harsh hydroformylation conditions are typically higher in temperature and longer contact times in the reaction zone and in the separation zone. These conditions tend to promote heavies formation such that harsher vaporizer conditions (higher temperature, lower pressure) are needed to avoid heavies buildup in the catalyst solution. In addition, ligand degradation from hydrolysis or alcoholysis (often promoted by the build up of acids) are increased under these conditions. Rhodium-promoted side reactions (e.g., ligand fragmentation) are also observed. Rhodium clustering and colloid formation can be observed which leads to inactive rhodium species. All of these factors promote catalyst deactivation and ligand loss (especially for hydrolysable phosphites).

It has been surprisingly found that an organic nitrogen compound when added to the hydroformylation reaction fluid may reduce the rate of loss of catalytic activity. Without wishing to be bound to any exact theory or mechanistic discourse it is believed that the encountered slow loss in catalytic activity of triorganophosphorous-promoted metal hydroformylation catalysts is due at least in part to the harsh conditions such as employed in the separation and recovery of the aldehyde product from its reaction product fluid. For instance it has been found that when a triarylphosphine-promoted rhodium catalyst is placed under harsh conditions such as high temperature and low carbon monoxide partial pressure such as occur in a vaporizer, that the catalyst deactivates at an accelerated pace with time, due most likely to the formation of an inactive or less active rhodium species, which may also be susceptible to precipitation under prolonged exposure to such conditions. Such evidence is also consistent with the view that the active catalyst which under hydroformylation conditions is believed to comprise a complex of rhodium, triarylphosphine, carbon monoxide and hydrogen, losses at least some of its coordinated carbon monoxide ligand during harsh conditions such as exist during separation, e.g., vaporization, which provides a route for the formation of such catalytically inactive or less active rhodium species as discussed above. As disclosed in U.S. Pat. No. 5,731,472 and US 2015/0376101, it is believed the free heterocyclic nitrogen compound serves as a replacement ligand for the lost carbon monoxide ligand thereby forming a neutral intermediate metal, e.g., rhodium, species comprising a complex of metal, triarylphosphine, the heterocyclic nitrogen compound and hydrogen during such separation under harsh conditions such as exist in a vaporizer, thereby preventing or minimizing the formation of any such above mentioned catalytic inactive or less active rhodium species. It is further theorized that the maintenance of catalytic activity, or the minimization of its deactivation, throughout the course of such continuous liquid recycle hydroformylation is due to regeneration of the active catalyst from said neutral intermediate rhodium species in the reactor (i.e. hydroformylation reaction zone) of the particular hydroformylation process involved. It is believed that under the higher syn gas pressure hydroformylation conditions in the reactor, the active catalyst complex comprising metal, e.g., rhodium, triarylphosphine, carbon monoxide and hydrogen is regenerated as a result of some of the carbon monoxide in the reactant syn gas replacing the heterocyclic nitrogen ligand of the recycled neutral intermediate rhodium species. That is to say, carbon monoxide having a stronger ligand affinity for rhodium, replaces the more weakly bonded heterocyclic nitrogen ligand of the recycled neutral intermediate rhodium species that was formed during vaporization separation as mentioned above, thereby reforming the active catalyst in the hydroformylation reaction zone. Similar phenomenon may also be occurring with phosphites. In any event, regardless of the specific mechanism involved regarding the formation of an intermediate rhodium species and/or the regeneration of active catalyst, it should be sufficient to note, that the use of such free heterocyclic nitrogen compounds in accordance with this invention is considered to be excellent means for preventing or minimizing catalytic activity loss of triorganophosphorous-promoted metal, e.g., rhodium, hydroformylation catalysts due to harsh conditions such as encountered in vaporization separation of the aldehyde product from its reaction production fluid.

The heterocyclic nitrogen compounds that are suitable for this application include diazoles, triazoles, diazines, and triazines. These are described in U.S. Pat. No. 5,731,472, for example. Illustrative of such diazine compounds are pyridazine, pyrimidine, pyrazine, and the like. The most preferred heterocyclic nitrogen compounds are the benzimidazole and benztriazole derivatives and most of all is benzimidazole and benztriazole.

Accordingly the free heterocyclic nitrogen compounds which are employable herein are well known compounds as are methods for their preparation and in many instances are readily available commercially. Moreover it is to be understood that while it may be preferred to employ only one free heterocyclic nitrogen compound at a time in any given hydroformylation process, if desired, mixtures of two or more different free heterocyclic nitrogen compounds may also be employed in any given process. Illustrative of suitable substituted and unsubstituted heterocyclic nitrogen compounds include those permissible substituted and unsubstituted heterocyclic nitrogen compounds described in Kirk-Othmer, *Encyclopedia of Chemical Technology*, Fourth Edition, 1996, the pertinent portions of which are incorporated herein by reference.

Moreover the amount of such free heterocyclic nitrogen compounds employable in any given process of this invention need only be that minimum amount necessary to furnish the basis for at least some minimization of such catalyst deactivation as might be found to occur as a result of carrying out an identical metal catalyzed hydroformylation process under essentially the same conditions, in the absence of any free heterocyclic nitrogen compound during harsh conditions such as vaporization separation of the aldehyde product. Amounts of such free heterocyclic nitrogen compounds ranging from about 0.001 up to about 10 weight percent, or higher if desired, based on the total weight of the hydroformylation reaction product fluid to be distilled should be sufficient for most purposes. It is of course to be understood that as the aldehyde product is distilled from the hydroformylation product fluid, the concentration of the non-volatilized components therein, e.g. the catalyst and free heterocyclic nitrogen compound, will increase accordingly. Thus the upper amount of free heterocyclic nitrogen compound is governed primarily by its solubility limit in the non-volatilized liquid rhodium catalyst containing residue obtained after such vaporization separation of the aldehyde product, i.e., distillation removal of as much of the aldehyde product desired. Such amounts of the free heterocyclic nitrogen compound employable herein will also depend in part upon the particular rhodium catalyst employed and the distillation temperature for recovering the aldehyde product, as well as the particular free heterocyclic nitrogen compound itself. In general preferred minor amounts of the free heterocyclic nitrogen compound present during the distillation of the desired aldehyde product from the metal-organophosphine catalyst containing product fluids of this invention may range from about 0.05 to about 5 weight percent based on the total weight of the hydroformylation reaction product fluid to be distilled.

The addition of the free heterocyclic nitrogen compound employable in this invention to the reaction product fluid from which the aldehyde product is to be distilled may be carried out in any suitable manner desired. For instance, the free heterocyclic nitrogen compound may be added to the hydroformylation reaction product fluid that has been removed from the reaction zone and at any time prior to or during the distillation of the aldehyde product therefrom. However, since the free heterocyclic nitrogen compound chosen to be used should not have any substantial detrimental affect on the hydroformylation reaction per se, the free heterocyclic nitrogen compound may be added directly to the hydroformylation reaction medium in the reaction zone and allowed to remain in solution throughout the entire hydroformylation process. Indeed, it may be desirable to add the free heterocyclic nitrogen compound to the precursor catalyst solution to be employed so that the free heterocyclic nitrogen compound is present right from the start of the hydroformylation process.

The amount of organic nitrogen compound that may be present in the reaction fluid is typically sufficient to provide a concentration of at least 0.0001 moles of free organic nitrogen compound per liter of reaction fluid. In general, the molar ratio of organic nitrogen compound to total organophosphorous ligand (whether bound or present as free organophosphorous ligand) is at least 0.01:1 and even more preferably at least 0.5:1. Organic nitrogen compound: organophosphorous ligand molar ratios of from 1:1 to 5:1 should be sufficient for most purposes.

An additional problem observed, mainly with hydrolysable organophosphorous ligands such as the organophosphites, is the acid-catalyzed hydrolysis which ultimately leads to phosphorous acid. The use of an aqueous buffer solution, such as in an extraction system, to prevent and/or lessen hydrolytic degradation of an organophosphite ligands and deactivation of a metal-organophosphite ligand complex is well-known and is disclosed, e.g., in U.S. Pat. Nos. 5,744,649, 5,741,944 and 5,741,942 and PCT Publication No. WO2013/184350. Such buffer systems and/or methods for their preparation and use in hydroformylation systems are well known in the art. Mixtures of buffers may be employed.

Other acid mitigation processes may also be employed such as epoxide addition, described in US Patent Publication Nos. 2003/0018220 and 2012/0172630, and PCT Publication No. WO2014/051975A1. The addition of water soluble amines such as trialkanolamines can also be used as described in PCT Publication No. WO2015/153070A1. Success in removing phosphorus acidic compounds from the reaction fluid may be determined by measuring the rate of degradation (consumption) of the organophosphorous ligand present in the hydroformylation reaction medium. The consumption rate can vary over a wide range, e.g., from <0.6 up to 5 grams per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., <0.5 grams of ligand per liter per day, and more preferably <0.1 grams of ligand per liter per day, and most preferably <0.06 grams of ligand per liter per day. As the neutralization and extraction of phosphorus acidic compounds into the aqueous buffer solution proceeds, the pH of the buffer solution will slowly decrease.

The extraction process can be carried out in a continuous manner, in a batch mode, or on a "as needed" basis. For example, a slip stream taken from the recycle line from the vaporizer can be treated then returned to the recycle line to be sent to the reaction zone. Alternatively, the entire reactor contents can be treated in a periodic batch extraction during a routine shutdown.

After the product-catalyst separation step in step (c), the resulting crude oxygenate stream is optionally degassed to remove unreacted CO prior to being subjected to hydrogenation to the alcohol. The crude aldehyde may still contain unreacted olefin as well as alkane depending on the degassing process, but these can be tolerated in the next processing step, hydrogenation.

The hydrogenation may be done via conventional process using conventional catalysts. Hydrogenation catalysts are typically supported transition metal-based catalysts employing nickel, copper, copper/zinc, chromium, platinum, palladium, cobalt, rhodium, and/or molybdenum and mixtures thereof. Reduced metal oxides (such as CuO and ZnO) and molybdenum sulfide catalysts can also be used. The supports are typically carbon, silica, alumina, and silica-alumina. Typical processes are described in U.S. Pat. Nos. 4,960,960 and 5,093,535. For example, vapor phase hydrogenation or liquid phase hydrogenation processes (or both including in series) can be used to produce the alcohol mixture. In general, ethers and esters are formed during step (b) hydroformylation but such reactions are often also observed during hydrogenation. In contrast to other uses for the resulting alcohols, the presence of such derivatives is not detrimental to the use of the hydrogenated stream in gasoline additives. Thus, harsher hydrogenation conditions or less expensive hydrogenation catalysts can be advantageously used to effect high conversion and to minimize recycle of unreacted aldehyde. Since the esters and ethers are useful in the gasoline additive application, extensive refining and recycling are not required thus saving capital and energy costs.

Figure 1B:
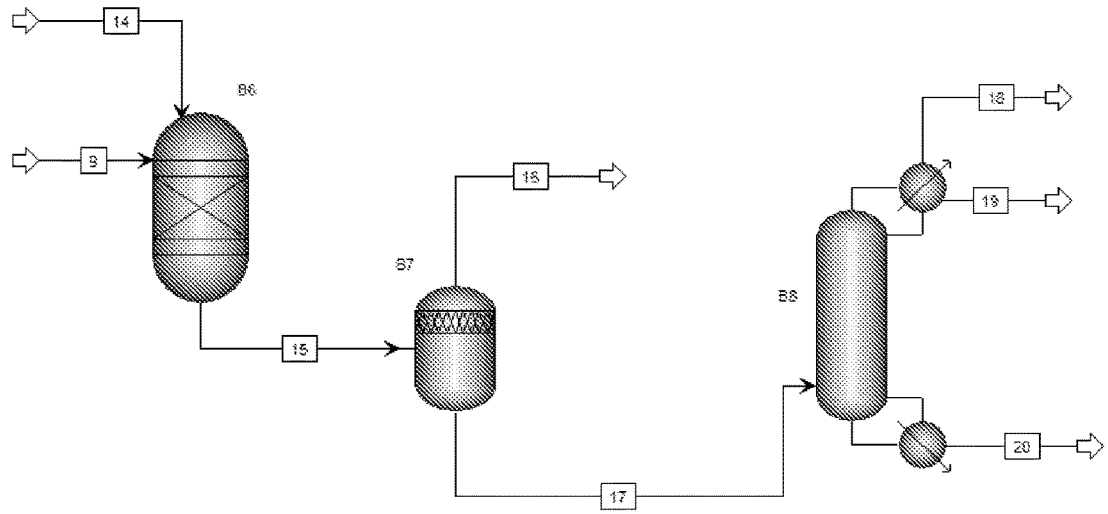

FIGS. 1A and 1B is represent a flow sheet illustrating a system for performing a process according to one embodiment of the present invention. It should be understood that other systems, equipment configurations, and streams could be utilized to perform other embodiments of processes of the present invention as disclosed herein. In that regard, while some alternative configurations are disclosed in discussing FIGS. 1A and 1B below, other alternatives are also possible that would likewise be considered embodiments of the present invention.

Starting with FIG. 1A, an olefin-containing feed stream (1) and a synthesis gas feed stream (2) are fed to one or more reactors (B1), or a single multi-stage reactor. In the presence of catalyst within the reactor(s) (B1), the hydroformylation reaction occurs. A combined stream reactor product and catalyst (4) is fed to a separation unit (B3), where the catalyst (5) is separated from the reaction products and unreacted components contained in the feed (7). Hydroformylation catalyst (5) is continually recycled back to the reactor(s) (B1). To facilitate separation of the catalyst from the reaction products and unreacted components contained in the feed, a stripping gas (6) can optionally be fed to the separation unit (B3). Alternatively, a vent gas (3) from the hydroformylation reactor(s) (B1), either alone or in combination with the stripping gas (6), can be fed to the separation unit (B3) and used as the stripping gas.

The gaseous stream (7) leaving the separation unit (B3) passes through a condenser (B4) to provide a non-condensed stream (8) and a stream comprised predominantly of hydroformylation products (9).

The non-condensed stream (8) from the separation unit (B3) can be routed directly to a control source as a low pressure vent stream. Optionally, in some embodiments, the non-condensed stream (8) from the separation unit (B3) can be pressurized using a compressor (B2) into a high pressure vent stream (11). This stream (11) can be routed to additional equipment (not shown) where the alkane is recovered and recycled back to other refinery operations, or can be sold as a chemical product. The stream (11) can also be sent to a control source as a high pressure vent stream. If the stream (11) contains a significant amount of unreacted olefin, part or all of the stream can be routed back to the hydroformylation reactor(s) (B1) for further processing as shown with stream (10). This stream (11), or a portion thereof, can also be fed to the separation unit (B3) and used as a stripping gas to facilitate separation of the hydroformylation products from the catalyst (not shown).

The stream comprised predominantly of hydroformylation products (9) is sent downstream for further processing into an oxygenate additive for gasoline as discussed more in connection with FIG. 1B. If necessary, impurities can be removed from this stream prior to further processing steps (not shown).

Referring now to FIG. 1B, the stream comprised predominantly of hydroformylation products (9) from FIG. 1A and a hydrogen stream (14) are fed to one or more hydrogenation reactors (B6). Following the one or more hydrogenation reactors (B6), a product stream (15) is optionally cooled, and then separated in separator (B7) into a stream comprised predominantly of hydrogenation products (17) and a stream comprising unreacted hydrogen, unreacted oxygenates, other unreacted components, and product (16) prior to being fed to a distillation column (B8). In the distillation column (B8), water (19) and low boiling impurities (18) are separated from an oxygenate product stream (20) intended for use as a fuel additive in gasoline. This stream (20) comprises predominantly alcohols, ethers, esters, and combinations thereof. While not shown, further processing of this stream in subsequent steps is possible and can result in a portion of the oxygenate product being removed prior to addition into the gasoline pool. The hydrogenation flowsheet shown in FIG. 1B is just one option that can be used to convert aldehydes into alcohols and other hydrogenation products, and is not meant to limit alternative processing possibilities in any way.

Some embodiments of the invention will now be described in detail in the following Examples.

EXAMPLES

General Procedure

A liquid recycle reactor system is employed that consists of two 1 liter stainless steel stirred tank reactors connected in series. Each reactor is equipped with a vertically mounted agitator and a circular tubular sparger located near the bottom of the reactor. Each sparger contains a plurality of holes of sufficient number and size to provide the desired gas flow and mixing into the liquid in the reactor. The spargers are used for feeding the olefin and/or syngas to the reactor, and can also be used to recycle unreacted gases to each reactor. Each reactor has a silicone oil shell as a means of controlling reactor temperature. Reactors 1 and 2 are further connected via lines to transfer any unreacted gases and lines to allow a portion of the liquid solution containing aldehyde product and catalyst to be pumped from reactor 1 to reactor 2. Hence, the unreacted olefin of reactor 1 is further hydroformylated in reactor 2. Each reactor has a liquid level controller for maintaining the desired liquid level. Reactor 2 has a vent for removal of unreacted gases.

A portion of the liquid reaction solution is continuously pumped from reactor 2 to a vaporizer, which consists of a heated vessel at reduced pressure. The resulting vapor/liquid stream from the vaporizer is sent to a gas-liquid separator located at the bottom of the vaporizer, where vaporized aldehyde is separated from the non-volatile components of the liquid reaction solution. The vaporized aldehyde product is condensed and collected in a product receiver. A liquid level controller controls the liquid level in the vaporizer. The liquid from the vaporizer containing unreacted aldehyde, heavies and catalyst is recycled to the Reactor 1.

Example 1 and Comparative Example

The above equipment was employed to study the conversion and catalyst stability of a catalyst composed of rhodium and tris(2,4-di-tert-butylphenyl)phosphite with a low-purity propylene feed (72 mole % purity). The reactor and vaporizer conditions are given in Table 1 after establishing stable operation. The testing period was over a week long to establish and confirm stable operation and to assess catalyst stability. Rhodium loss was determined by atomic absorption (AA) determination of the catalyst solution. Later the same catalyst solution was used on a high purity propylene feed (99.8 mole %) to allow a direct comparison with the lower purity feed operating at the comparable reactor conditions.

|  | Low Purity Propylene | Polymer grade Propylene Feed |
|---|---|---|
| Feed Composition |  |  |
| Propylene, mole % | 72.2 | 99.8 |
| Reactor Conditions | Rx1/Rx2 | Rx1/Rx2 |
| Pressure, (psig) | 262/215 | 149.5/137.2 |
| Temperature, ° C. | 65/65 | 65/65 |
| Average Rhodium over both Reactors, ppmw | 53 | 64 |
| Average Ligand (free) wt. % over both Reactors | 0.74 | 0.41 |
| Partial Pressures, psi |  |  |
| Hydrogen | 42/33 | 76/77 |
| Carbon Monoxide | 58/58 | 51/50 |
| Propylene | 79/21 | 22/9 |
| Propane | 77/90 | 0.3/0.3 |
| Overall Catalyst Performance |  |  |
| Turnover/second (Rh basis) | 1.4 | 1.0 |
| Olefin conversion (%) | 89 | 95 |
| Overall N/I | 1.4 | 1.3 |
| Vaporizer Conditions: |  |  |
| Vaporizer Oil out Temp, C. | 90 | 104 |
| Pressure, psia | 21.2 | 17.0 |
| Rhodium loss (ppm/day) | 0.1 | 0.3 |

The data show that the higher purity polymer grade propylene feed requires a higher vaporizer temperature (104° C.) as compared to the lower purity propylene feed (90° C.) to achieve the desired product separation. Prior studies have shown that higher product-catalyst separation temperatures in the vaporizer result in higher rhodium losses due to clustering. In the lower purity propylene case, the presence of propane feed facilitates the product/catalyst separation via gas stripping effect which allows a lower vaporizer operating temperature and hence a substantially lower catalyst degradation rate. In addition, the above data show that a low purity propylene feed can be converted to an aldehyde stream having a low N/I ratio, which when converted to alcohols, can be suitable for use as a gasoline additive.

What is claimed is:

1. A process for converting olefins to alcohols, ethers, or combinations thereof that are suitable for use as a gasoline additive, the process comprising:
   (a) receiving a feed stream, wherein the feed stream comprises one or more olefins having 2 to 5 carbon atoms in an amount of up to 80% by weight based on the weight of the feed stream, wherein the feed stream comprises at least 50% by weight ethylene, propylene, and/or butene and at least 15% by weight alkanes:
   (b) hydroformylating the feed stream in the presence of a catalyst to convert at least 80% of the olefins from the feed stream to oxygenates, wherein the catalyst comprises rhodium and at least one of organophosphorous ligand:
   (c) separating a product stream from step (b) into an oxygenate stream and a stream comprising unreacted olefins, inerts, the catalyst, and the remaining oxygenates; and
   (d) treating the oxygenate stream to convert a plurality of the oxygenates into at least one of an alcohol, an ether, or combinations thereof having at least 3 carbon atoms, wherein at least 25 weight percent of the alcohols and ethers having at least 3 carbon atoms are branched based on the total weight of the alcohols and ethers having at least 3 carbon atoms, and wherein the alcohols, ethers, or combination thereof is suitable for use as a gasoline additive.

2. The process of claim 1, wherein the feed stream comprises at least 50% propylene.

3. The process of claim 1, wherein the oxygenate stream in step (c) comprises an aldehyde.

4. The process of claim 1, wherein treating the oxygenate stream comprises hydrogenation of the oxygenate into an alcohol.

5. The process of claim 1, wherein the oxygenates comprise an isobutyraldehyde and wherein treating the oxygenate stream comprises hydrogenation of the isobutyraldehyde into isobutyl alcohol or diisobutyl ether.

6. The process of claim 5, further comprising removing at least some of the alcohols and ethers after step (d).

7. The process of claim 5, further comprising adding a stream comprising the alcohols, the ethers, or the combination thereof after step (d) to gasoline.

8. The process of claim 5, wherein at least 90% of the alcohols from step (d) comprise alcohols having 3 to 6 carbon atoms.

9. The process of claim 5, wherein at least 40% of the alcohols and ethers having at least 3 carbon atoms are branched based on the total weight of the alcohols and ethers having at least 3 carbon atoms.

10. The process of claim 5, wherein the catalyst comprises rhodium and at least one of triorganophosphite, dicyclohexylphenylphosphine, cyclohexyldiphenylphosphine, triphenylphosphine, 2,6-di-t-butyl-4-methylphenyl-1,1'-biphenyl-2,2'diylphosphite, tris(2,4-di-tert-butylphenyl) phosphite, or 4,8-bis(1,1-dimethylethyl)-6-[2-(1,1-dimethylethyl)-4-methoxyphenoxy]-2,10-dimethoxydibenzo WA [1,3,2]dioxaphosphepin.

11. The process of claim 1, wherein the feed stream is hydroformylated using a rhodium-based catalyst with a reactivity of greater than 0.5 turnovers/second on a rhodium-atom basis.

12. The process of claim 5, wherein the feed stream comprises one or more alkanes and wherein during the separation step (c) alkanes from the feed stream facilitate the separation, or wherein the separation step (c) comprises a stripping gas vaporizer wherein alkanes from the feed stream are used to facilitate the separation.

13. The process of claim 12, wherein the feed stream comprises at least 20 weight percent alkanes, based on the weight of the feed stream.

14. The process of claim 1, wherein at least 90% of the olefins in the feed stream are converted to oxygenates in the hydroformylation of step (b).

* * * * *